US011707382B1

(12) United States Patent
Urich

(10) Patent No.: US 11,707,382 B1
(45) Date of Patent: *Jul. 25, 2023

(54) CATARACT SURGICAL DEVICE VIBRATION PROFILE

(71) Applicant: Alex Urich, Coto de Caza, CA (US)

(72) Inventor: Alex Urich, Coto de Caza, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/081,511

(22) Filed: Dec. 14, 2022

Related U.S. Application Data

(63) Continuation-in-part of application No. 17/866,206, filed on Jul. 15, 2022, now Pat. No. 11,576,815.

(51) Int. Cl.
*A61B 17/00* (2006.01)
*A61F 9/007* (2006.01)

(52) U.S. Cl.
CPC ...... *A61F 9/00745* (2013.01); *A61B 2017/00172* (2013.01); *A61B 2017/00185* (2013.01); *A61B 2017/00194* (2013.01); *A61B 2017/00973* (2013.01); *A61B 2217/005* (2013.01); *A61B 2217/007* (2013.01)

(58) Field of Classification Search
CPC ....... A61F 9/00745; A61B 2017/00172; A61B 2017/00185; A61B 2017/00194; A61B 2017/00973; A61B 2217/005; A61B 2217/007
USPC .......................................................... 606/16
See application file for complete search history.

(56) References Cited

U.S. PATENT DOCUMENTS

| 5,112,300 | A |   | 5/1992  | Ureche            |
|-----------|---|---|---------|-------------------|
| 5,213,569 | A |   | 5/1993  | Davis             |
| 5,431,664 | A | * | 7/1995  | Ureche ................ B06B 1/0253 606/171 |
| 6,884,252 | B1|   | 4/2005  | Urich et al.      |
| 9,788,998 | B2|   | 10/2017 | Kadziauskas et al.|
| 2009/0069712 | A1|   | 3/2009  | Mulvihill      |
| 2013/0285758 | A1| * | 10/2013 | Aldridge ................ A61B 18/04 332/108 |

* cited by examiner

*Primary Examiner* — Aaron F Roane
(74) *Attorney, Agent, or Firm* — Kenneth Altshuler

(57) ABSTRACT

Disclosed is a surgical instrument for cataract eye surgery. The instrument generally includes a handpiece that delivers sub-ultrasonic and ultrasonic vibrations in either a continuous emulsification mode or with on-off pulses that dynamically drive a hollow needle in either a pulsed fragmentation mode or a pulsed emulsification mode. The pulsed fragmentation mode is efficient at cutting lens tissue and the pulsed emulsification mode is efficient in emulsifying the cut lens tissue. The pulsed modes manage heat buildup from becoming excessive in the eye during the cataract surgery. While in the pulsed fragmentation mode, the hollow needle is never given the chance to vibrate at an established resonant frequency of the handpiece due to the short on-off period. In contrast, the pulsed emulsification mode has a long enough on-off period to permit an ultrasonic resonant frequency in the handpiece to develop, which drives the hollow needle at a higher energy than the pulsed fragmentation mode.

20 Claims, 6 Drawing Sheets

CATARACT SURGICAL DEVICE VIBRATION PROFILE

CROSS-REFERENCE TO RELATED APPLICATIONS

This application is a Continuation-In-Part Patent Application which claims priority to and the benefit of U.S. patent application Ser. No. 17/866,206 entitled Fragmentation and Emulsification Modes in a Cataract Surgical Device filed on Jul. 15, 2022.

FIELD OF THE INVENTION

The present invention relates generally to the field of medical devices used in eye surgery, and more particularly to tools and methods applied to cataract surgical procedures.

BACKGROUND

Needles that are actuated at ultrasonic frequencies may be used in various contemporary eye surgical procedures. For example, the lens of a human eye may develop a cataractous condition that affects a patient's vision. Cataractous lenses are sometimes removed and replaced in a procedure commonly referred to as phacoemulsification. Phacoemulsification procedures are typically performed with a front/back cylinders that actuates a needle at ultrasonic frequencies. The needle is inserted through an incision in the cornea up to a desired insertion depth, and then ultrasonic actuation at one specific frequency is used to break the lens within the lens capsule of the eye. The broken lens may be removed through an aspiration line that is coupled to the front/back cylinders, drawing irrigation fluid and aspirated tissue from a hollow passage through the needle. It is to improvements in ultrasonic actuation of a phacoemulsification needle that embodiments of the present invention are generally directed.

SUMMARY

The present invention is directed to embodiments of a cataract surgical device and circuitry that can switch between a fragmentation mode and an emulsification mode. The different duty cycle modes produce different surgical effects that are used to break-up and remove a cataractous lens.

Certain embodiments of the present invention can therefore include a cataract surgical instrument comprising a handpiece that includes a transducer comprising a front/back cylinders, a horn, and a PZT driver. When the PZT driver is in an on-state, it receives input power that generates output vibrations in an ultrasonic frequency, thereby driving vibrations in the transducer and ultimately the needle tip, which is used as the cutting tool for the cataractous lens and when in an off-state, the PZT driver does not receive the input power. The ultrasonic frequency is at a resonant frequency of the handpiece to be able to produce high (to near maximum at that frequency) amplitude vibrations in the needle tip based on the voltage provided. A hollow needle is attached to the horn. The hollow needle extends to a free distal tip that is configured to penetrate a human eye. A power driver provides the input power to the PZT driver at either 1) a constant on state, or 2) a plurality of on-off pulses. The on-off pulses are either in a pulsed fragmentation mode or a pulsed emulsification mode. The on-off pulses each have a duty cycle that is the same in both the pulsed fragmentation mode and pulsed emulsification mode. The duty cycle is defined by on-time of the on-state divided by a duty cycle period. For example, the duty cycle period is a sum of the on-time and off-time of the off-state (on-time+off-time). The pulsed fragmentation mode has a shorter duty cycle period than the pulsed emulsification mode.

Yet another embodiment of the present invention envisions a device for cataract surgery generally comprising a handpiece that includes a hollow needle and a transducer. The transducer comprising front and back cylinders, a horn, and a PZT driver. When the PZT driver is in an on-state, it receives input power (current) that generates output vibrations in an ultrasonic frequency but when the PZT driver is in an off-state, it does not receive any input power. In this embodiment, the ultrasonic frequency is at a resonant frequency of the handpiece, but in other embodiments the ultrasonic frequency is at a resonant frequency of the transducer. The horn can be connected to the hollow needle, which extends to a free distal tip. The hollow needle is configured to penetrate nothing other than a human eye. A power driver can be connected to the PZT driver, which can deliver a plurality of on-off pulses of electrical voltage to the PZT driver. Each of the on-off pulses are defined by a duty cycle period, which is a sum of on-time in the on-state and off-time in the off-state, and a duty cycle, which is the on-time divided by the duty cycle period (on-time/(on-time+off-time)). A manual duty cycle period adjuster, such as a foot pedal, can be used to increase the duty cycle period (of the plurality of on-off pulses) from that which does not generate an ultrasonic resonance in the handpiece to that which does generate the ultrasonic resonance in the handpiece. In this embodiment, the plurality of on-off pulses all has the same duty cycle while the device is in operation.

Still yet another embodiment of the present invention envisions a method for using a cataract surgical instrument. The cataract surgical instrument generally comprises a handpiece that includes a transducer comprising a front/back cylinders, a horn, and a PZT driver that when in an on-state receives input power that generates output vibrations in a transducer ultrasonic resonant frequency and when in an off-state does not receive the input power. The handpiece further including a hollow needle that is attached to the horn, wherein the hollow needle extends to a free distal tip. The method envisions a step for applying voltage on-off pulses to the PZT driver in either a pulsed fragmentation mode or a pulsed emulsification mode, wherein each of the on-off pulses have a duty cycle that, in turn, has a duty cycle period. The duty cycle period is a sum of on-time in the on-state and off-time in the off-state and the duty cycle is the on-time divided by the duty cycle period. The duty cycle period is increased from a short duty cycle period to a long duty cycle period that is longer than the short duty cycle period via a manual duty cycle period adjuster. The pulsed fragmentation mode corresponds to the short duty cycle period and the pulsed emulsification mode corresponds to the long duty cycle period. The duty cycle does not change between the pulsed fragmentation mode and the pulsed emulsification mode. After the applying step, the voltage on-off pulses are changed to a continuous mode, which is when the on-state that is devoid of any of the voltage on-off pulses during the on-state.

DETAILED DESCRIPTION

Figure 1A:
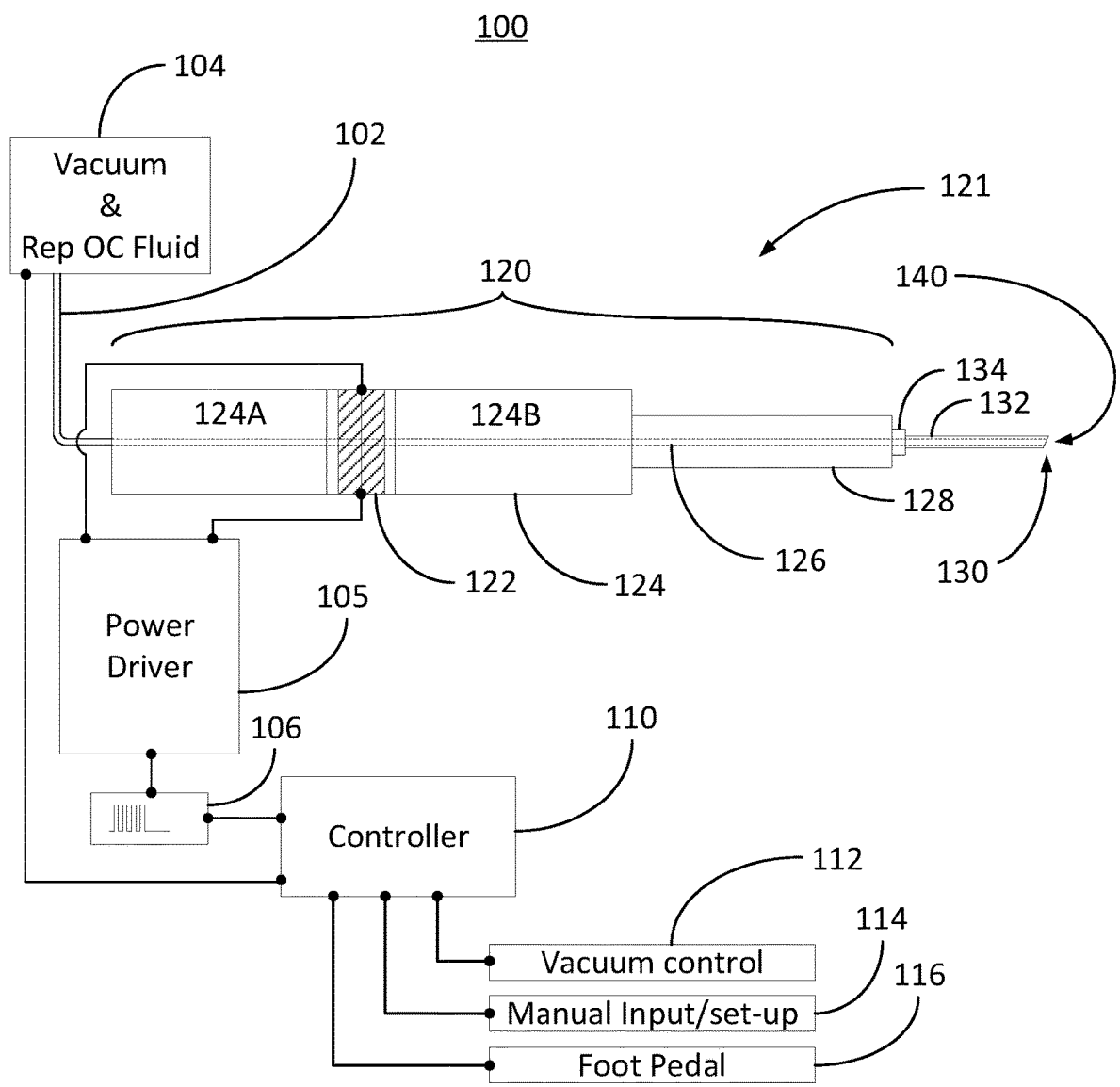
FIG. 1A is a block diagram of a cataract surgical arrangement consistent with embodiments of the present invention.

Initially, this disclosure is by way of example only, not by limitation. Thus, although the instrumentalities described herein are for the convenience of explanation, shown and described with respect to exemplary embodiments, it will be appreciated that the principles herein may be applied equally in other similar configurations involving the subject matter presented in the field of the invention. The phrases "in one embodiment", "according to one embodiment", and the like, generally mean the particular feature, structure, or characteristic following the phrase, is included in at least one embodiment of the present invention and may be included in more than one embodiment of the present invention. Importantly, such phases do not necessarily refer to the same embodiment. If the specification states a component or feature "may", "can", "could", or "might" be included or have a characteristic, that particular component or feature is not required to be included or have the characteristic. As used herein, the terms "having", "have", "including" and "include" are considered open language and are synonymous with the term "comprising". Furthermore, as used herein, the term "essentially" is meant to stress that a characteristic of something is to be interpreted within acceptable tolerance margins known to those skilled in the art in keeping with typical normal world tolerance, which is analogous with "more or less." For example, essentially flat, essentially straight, essentially on time, etc. all indicate that these characteristics are not capable of being perfect within the sense of their limits. Accordingly, if there is no specific +/− value assigned to "essentially", then assume essentially means to be within +/− 2.5% of exact. The term "connected to" as used herein is to be interpreted as a first element physically linked or attached to a second element and not as a "means for attaching" as in a "means plus function". In fact, unless a term expressly uses "means for" followed by the gerund form of a verb, that term shall not be interpreted under 35 U.S.C. § 112(f). In what follows, similar or identical structures may be identified using identical call-outs.

Some aspects of the present invention are directed to a surgical instrument for cataract eye surgery. The surgical instrument generally includes a handpiece that delivers vibrations in either a steady-state mode (continuous mode) with on-off pulses that dynamically drives a hollow needle in either a pulsed fragmentation mode or a pulsed emulsification mode. The pulsed fragmentation mode is a mode wherein the hollow needle is never given the chance to vibrate at an established resonant frequency of the handpiece due to the short on-off period. In contrast, the pulsed emulsification mode has a long enough on-off period to permit an ultrasonic resonant frequency in the handpiece to develop, which drives the hollow needle at a higher energy (ultrasonic vibration) than the pulsed fragmentation mode. While in pulsed fragmentation mode, the hollow needle is efficient at cutting lens tissue and the pulsed emulsification mode is efficient at emulsifying the cut lens tissue. The pulsed modes manage heat buildup from becoming excessive in the eye during the cataract surgery.

FIG. 1A is a block diagram of a cataract surgical arrangement 100 consistent with embodiments of the present invention. As shown, the cataract surgical arrangement 100 generally depicts an eye surgery handpiece (or simply "handpiece") 121 that is electrically coupled to a power driver 105 and physically coupled to a vacuum and replacement ocular fluid source 104 via a transfer tube 102. The power driver 105 is electrically coupled to a controller 110 as are the vacuum and replacement ocular fluid sources 104. The vacuum and replacement ocular fluid sources 104 can be in a single unit/element or in several different units/elements. In the present embodiment, the controller 110 includes at least a microprocessor and non-transitory memory (not shown) and other electronics that support computing and controlling functionality, known to those skilled in the art. The controller 110 can receive input from the vacuum and replacement ocular fluid source 104, a foot peddle 116 or manual actuator, it can be set up manually to have certain functionality, just to name several options.

With more detail to the handpiece 121, the present embodiment generally comprises a transducer 120 that includes a front/back cylinder 124, a piezoelectric crystal transducer (PZT) driver 122, and a horn 128. The handpiece 121 further includes a hollow needle 132 that is attached to the horn 128 via a threaded tip/needle hub 134. The needle 132 is defined by a substantially cylindrical portion between the tip hub 134 and the free distal tip 130. The substantially cylindrical needle 132 as defined herein is a hollow needle 132 that may not be a perfect cylinder, but rather may be something between a cylinder to a slight taper (such as a tape or under 5%, for example) with the diameter of the hollow needle 132 being larger at the tip hub 134 than at the free distal tip 130. The handpiece 121 additionally includes a metal shell that encapsulates the front/back cylinders 124, which an eye surgeon or operator can grip.

The free distal tip 130 of the hollow needle 132, which can be a hollow titanium needle or other suitable needle known to those skilled in the art, comprises an evacuation orifice 140 (i.e., an opening/aperture) that leads into an aspiration passageway/channel 126. The aspiration passageway/channel 126 extends through the center axis of the handpiece 121 to the vacuum source and replacement ocular fluid source 104 via a transfer tube 102. Hence, the evacuation orifice 140 located at the free distal tip 130 is in communication with the vacuum source and replacement ocular fluid source 104 via the transfer tube 102 and the aspiration channel 126.

In the present embodiment, the PZT driver 122 (not to be confused with the transducer 120, which includes the front/back cylinders 124, the horn 128 and the PZT driver 122) comprises a pair of PZT crystals that are connected by way of a center bolt (not shown) and sandwiched between a rear cylinder 124A and a front cylinder 124B of the front/back cylinders 124. The PZT driver 122 is one embodiment of a vibration generator that receives electrical power from the power driver 105.

During a cataract surgical procedure (while the handpiece 121 is in operation), a cataractous lens is broken into small particles by the combined cavitation effects and cutting action of the ultrasonically vibrating free distal tip 130 of the needle 132. Vibrating the needle 132 improves penetration into lens tissue of an eye, while the cavitation of the surrounding ocular liquid/fluid helps to emulsify or otherwise disintegrate cataractous lens tissue into small particles that can be easily aspirated, or sucked, along with ocular fluid away from the eye through the aspiration passageway 126. Replacement saline fluid from the replacement ocular fluid source 104 is transported along an infusion/irrigation pathway connected to the front/back cylinders 124 (not shown) and infused back into the eye to prevent the eye from collapsing.

Disintegrating cataractous lens tissue in a manner that can be aspirated away from the eye without burning or causing unwanted damage to the eye can be accomplished by driving the handpiece 121 in both a tissue fragmentation mode and in a tissue emulsification mode.

A tissue fragmentation mode is predominantly a sub-ultrasonic frequency vibration of the free distal tip 130. The sub-ultrasonic frequency is considered a "low" frequency herein. In the tissue fragmentation mode, cataractous lens tissue is essentially cut and fragmented without generating enough heat to burn the eye at the incision, which can occur with prolonged periods of time when the free distal tip 130 is ultrasonically vibrating. Also, while in tissue fragmentation mode, there is little, or no cavitation generated by the free distal tip 130. One drawback of fragmentation mode is that larger fragmented lens tissue can occlude or otherwise block the evacuation orifice 140 of the free distal tip 130 preventing broken up cataractous lens tissue from being sucked away. Another drawback of fragmentation mode is that harder cataractous lens material is not easily broken up in a manner that can be sucked away through the evacuation orifice 140.

In contrast, tissue emulsification mode causes cavitation in the ocular fluid causing the disintegration, or emulsification, of larger particles that were originally broken up in tissue fragmentation mode. The smaller emulsified particles are more easily sucked through the evacuation orifice 140 than the larger fragmented particles. Moreover, larger particles that cause a blockage, or occlusion, of the aspiration passageway 126 at the free distal tip 130 are easily broken up when the free distal tip 130 is ultrasonically vibrated in the tissue emulsification mode. Nonetheless, there are several drawbacks to tissue emulsification mode. For example, in addition to excessive heat generation during emulsification mode, those particles that are not readily sucked up through the evacuation orifice 140 can be pushed around or otherwise chased away from the free distal tip 130 of the vibrating needle 132 causing extended times to complete a cataract surgery procedure.

The effectiveness and speed of cataract surgery depends on the rate at which broken up and/or the emulsified lens tissue is removed from an eye, which involves balancing the amount of time a surgeon spends in both tissue fragmentation mode and tissue emulsification mode. In either fragmentation mode or emulsification mode, the surgeon may lose the broken-up particle requiring time spent maneuvering around the eye to reengage the particle to suck it away. Accordingly, certain embodiments of the present invention contemplate achieving either a fragmentation mode or an emulsification mode by employing a plurality of proportionally constant duty cycles at shorter or longer duty cycle time intervals.

Figure 1B:
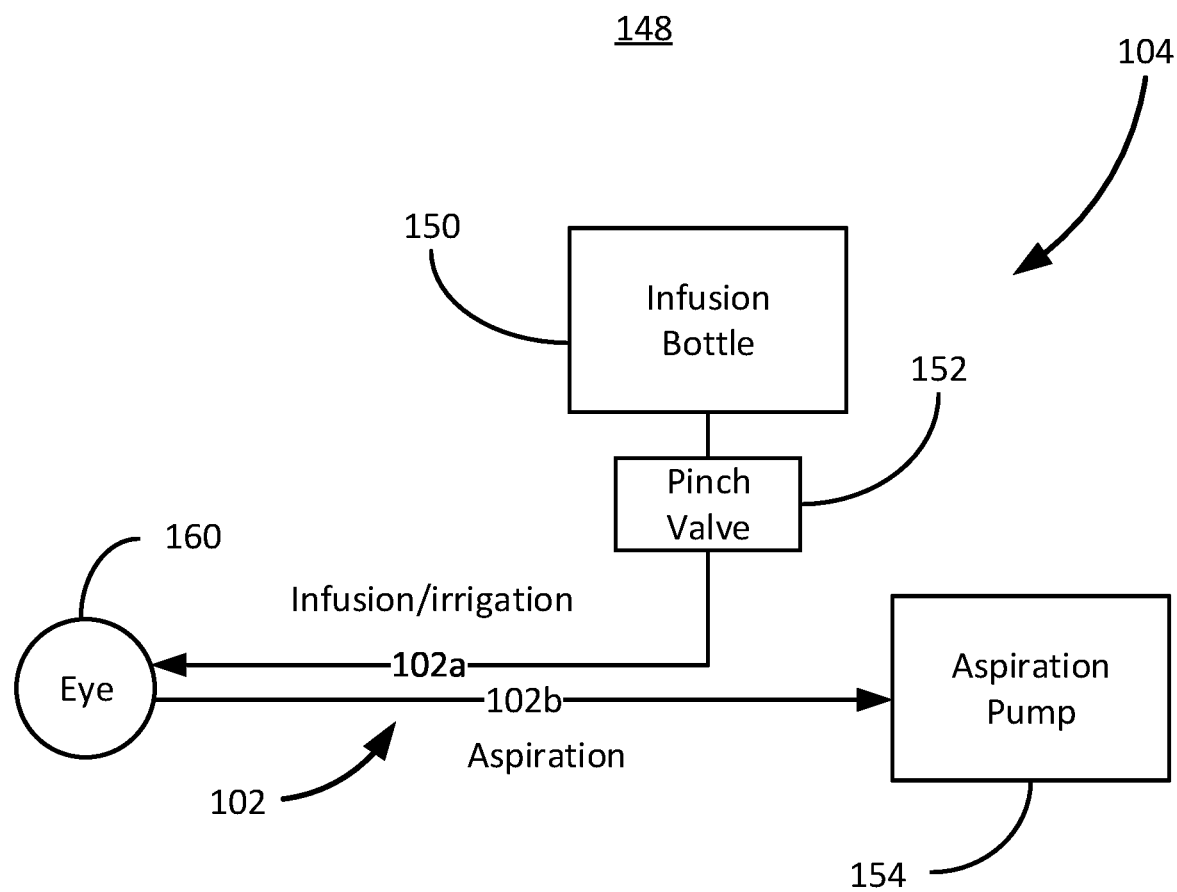
FIG. 1B is a block diagram of the vacuum and ocular replacement fluid source embodiment consistent with embodiments of the present invention.

FIG. 1B is a block diagram of the vacuum and ocular replacement fluid source embodiment 104 consistent with embodiments of the present invention. As shown, the vacuum and ocular replacement fluid source 104 includes an infusion bottle 150 filled with balanced salt solution (irrigation fluid) that is generally positioned between 100 cm to 130 cm above the eye 160 being operated on, or to a level that gravitationally provides balanced intraocular pressure (IOP) in the eye 160. In one embodiment, a pressurized fluid source may be employed in addition to or in place of an infusion bottle 150. TOP is generally between 10 mm Hg and 20 mm Hg and averages 15.5 mm Hg in a human eye 160. During a cataract surgery, a surgeon tries to keep the TOP above 20 mm Hg, especially after a vacuum surge. The replacement fluid in the infusion bottle 150 is generally comprised of an osmotically balanced salt solution that is compatible with the ocular fluid in the eye 160. The system 148 further comprises a pinch valve 152 that opens and closes an infusion/irrigation pathway 102a to the eye 160. An aspiration pump 154 sucks or otherwise pulls emulsified lens/ocular material from the eye 160 through the hollow opening 140 in the free distal tip 130 of needle 132. During an eye surgery procedure, the aspiration needle 132 is inserted through an incision in the anterior chamber of the eye 160 (at the cornea) up to and including an irrigation port (not shown). During an eye surgery, the needle 132 is vibrated in the sonic to ultrasonic frequency range to cut and break up lens material in the eye 160. The small pieces of the broken-up lens material and ocular fluid are sucked through the needle 132 away from the eye 160 along the aspiration passageway 102b by way of a vacuum generated by the aspiration pump 154. The aspiration pump 154 is configured to pull (vacuum) a specific volume of emulsified lens material at a particular rate from the eye 160. Generally, the aspiration rate is approximately 25 to 50 cc of fluid/minute. TOP is maintained with irrigation fluid (replacement fluid) that replaces the removed lens material at the same rate as the aspirated lens material. This is accomplished by leveraging the gravitational effects of positioning the infusion bottle 150 at an appropriate distance above the eye 160 to balance the pressure of the replacement fluid with the TOP. The irrigation fluid is discharged into the inside of the eye 160 through the irrigation port(s) while the irrigation ports are located inside of the eye 160. In other words, the irrigation fluid replaces the aspirated lens and ocular material at the same rate at which the lens and ocular material is removed from the eye 160 to maintain appropriate TOP, thus avoiding collapse of the anterior chamber of the eye 160. Hence, the irrigation flow rate into the eye 160 essentially equals the aspiration flow rate from the eye 160. The word essentially is used here to indicate that at some level, the flow rate is not exactly equal, but for all intents and purposes the two flow rates are more or less equal.

Figure 2A:
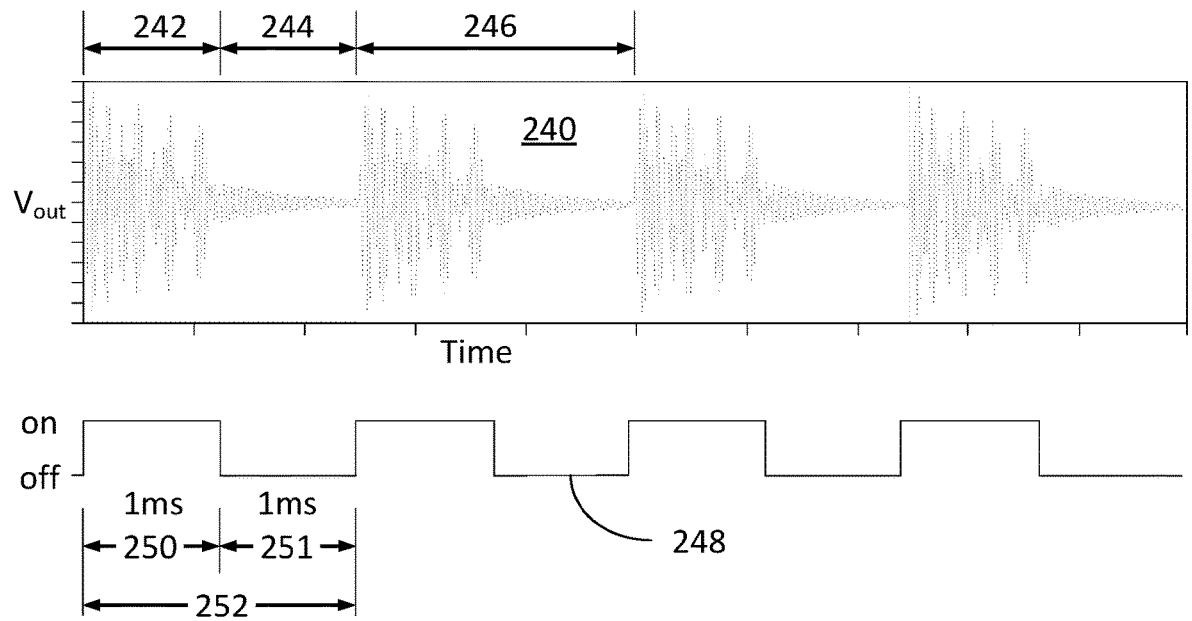
FIGS. 2A and 2B illustratively depict proportionally constant duty cycles at two different duty cycle periods consistent with embodiments of the present invention.
Figure 2B:
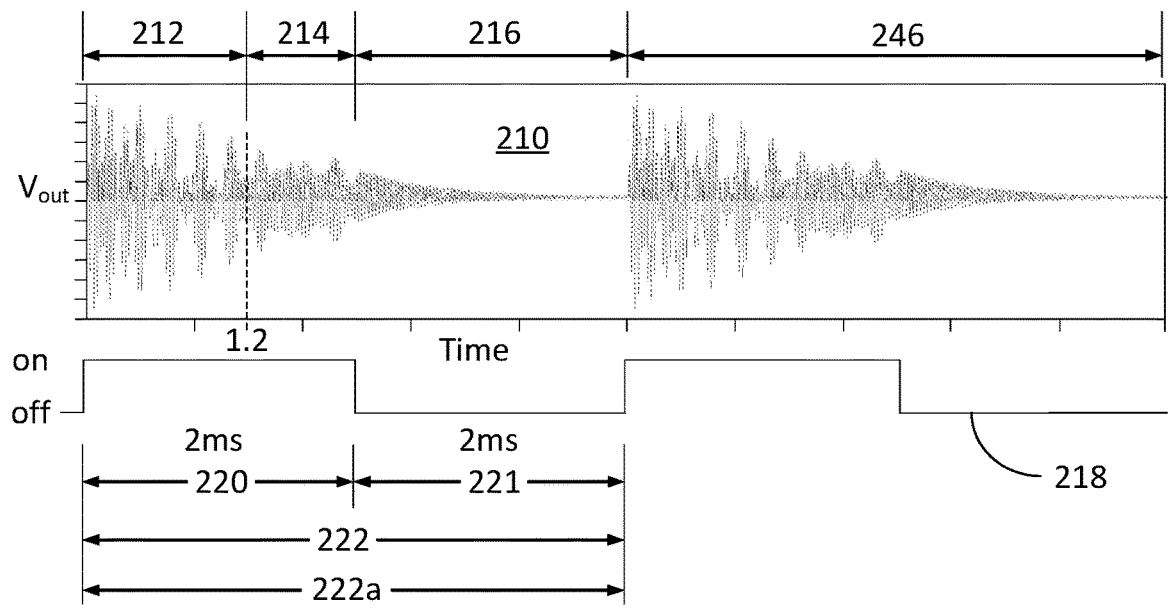

FIGS. 2A and 2B illustratively depict proportionally constant duty cycles at two different duty cycle periods (time intervals) consistent with embodiments of the present invention. By way of definition, a duty cycle is defined by the input voltage 'on-time' 220 divided by the 'total-time' 222 (on-time and off-time) of a single on-off pulse 246 (single on-off cycle). The input voltage being supplied by the power driver 105, or some other voltage source known to those having skill in the electrical arts. The time it takes to complete a single on-off pulse 246 is considered a duty cycle period, which is generically referred to herein as 222a, but exemplified as 222 or 252. The voltage on-time 220 or 250 is the time duration when voltage is applied to the PZT driver 122 via the power driver 105. In this example, each of the duty cycles in the upper plot of FIG. 2A and the lower plot of FIG. 2B are 0.5 or 50%, albeit having different duty cycle periods 222 and 252.

FIG. 2A depicts a duty cycle plot 240 comprising four on-off pulses 246, wherein each of the on-off pulses 246 have a duty cycle period 252 of 2 ms. The 2 ms. duty cycle period 252 comprises 1 ms. of applied voltage on and 1 ms. off. This is a duty cycle of 50%. The applied voltage, shown in the $V_{out}$ y-axis, is at an ultrasonic frequency that if left to develop will bring the transducer 120, and in some embodiments, the handpiece 121 into resonance (see established resonant frequency zone 214 of FIG. 2B). When voltage is first applied to the handpiece 121, vibration momentum must build before the handpiece 121 vibrates at a resonant frequency due to the physical properties of the handpiece 121 (e.g., mass and elasticity of the materials comprising the handpiece 121). The time it takes for the vibrations to reach or otherwise settle at resonance in the handpiece 121 is the settling time 212. Hence, the applied voltage to the PZT driver 122 does not bring the handpiece 121 into an established resonance 214 until after the settling time 212 is reached.

In the present example shown in FIG. 2A, the handpiece 121 never gets to an established resonant frequency 214 due to insufficient on-time 250 of 1 ms. that the voltage is applied to the PZT driver 122. Accordingly, over this sub-resonant frequency window 242, the hollow needle 132 does not go beyond a fragmentation mode (or essentially a fragmentation mode) because the handpiece 121 never reaches a resonance mode 214. The term "essentially" as used here is considered a condition that causes little to no cavitation of the ocular fluid inside of the eye, which means that any small effects of emulsification and cavitation are not significant enough for a surgeon to notice. Over the following 1 ms during the off-time 251 when there is no applied voltage to the PZT driver 122, the vibrations in the handpiece 121 decay towards zero, as shown by the vibration decay zone 244. The on-off pulses 246 with the 2 ms. duty cycle period 252 are repeated unless there is an external input to the power driver 105 from the controller 110, such as via an external input by the surgeon using a foot pedal or switch on the handpiece 121 or a change in vacuum pressure or fluid flow of the replacement ocular fluid from the sources 104, for example. In the event there is a need or desire to go into emulsification mode, the fragmentation mode duty cycle period 252 can be lengthened to generate an emulsification mode duty cycle period 222.

FIG. 2B depicts a duty cycle plot in pulsed emulsification mode on-off pulses 210 wherein an emulsification mode is obtained by lengthening the duty cycle period 222 sufficiently to permit the handpiece 121 to vibrate ultrasonically at resonant frequency. As shown in FIG. 2B, there are two on-off pulses 246, each having a duty cycle period 252 of 4 ms. The plot of FIG. 2A is lined up with the plot of FIG. 2B. Each 4 ms. duty cycle period 222 comprises 2 ms. of applied voltage 'on' 220 and 2 ms. with the voltage turned, or cycled, 'off' 221 (hence, maintaining the duty cycle of 50% shown in plot of FIG. 2A). The applied voltage, shown in the $V_{out}$ y-axis, is at an ultrasonic frequency that is permitted to develop over time to create a resonant mode in the handpiece 121 (i.e., the ultrasonic frequency resonates the handpiece 121). The applied voltage to the PZT driver 122 does not bring the handpiece 121 into an established resonant vibration 214 until after a settling time 212 from when the voltage to the PZT driver 122 is first applied. The settling time 212 allows the handpiece 121 to build the necessary momentum needed to establish resonant vibration 214 in the handpiece 121. In the present example, the handpiece 121 takes 1.2 ms. to reach an established resonant frequency 214 from the initial application of voltage to the PZT driver 122, shown at the dashed line. Established resonance 214 vibrates, or otherwise drives, the hollow needle 132 in the tissue emulsification mode, which in this example is for 0.8 ms. In contrast, the handpiece 121 is in a non-resonance mode during the settling time 212 (time to settle into resonance), which drives the hollow needle 132 in essentially only a fragmentation mode. Over the following 2 ms. during the off-time 221 when there is no applied voltage to the PZT driver 122, there is a vibration decaying window 216, wherein the vibrations in the handpiece 121 decay to nearly zero. The 4 ms. duty cycle period 222 of the on-off cycle 246 is repeated unless there is an external input to the power driver 105 from the controller 110, such as an external input by the surgeon using a foot pedal or switch on the handpiece 121, or a change in vacuum pressure or fluid flow of the replacement ocular fluid from the sources 104, for example.

Certain embodiments envision that the hollow needle 132 comprises a mass that is insignificant as compared to the handpiece 121. Accordingly, simply driving the transducer 120 into a resonant mode is all that is needed to drive the entire handpiece 121 into resonance. In these embodiments, the description of FIGS. 2A and 2B can equally be applied to driving the transducer 120 into sub-resonance for fragmentation mode or resonance for emulsification mode.

Figure 3:
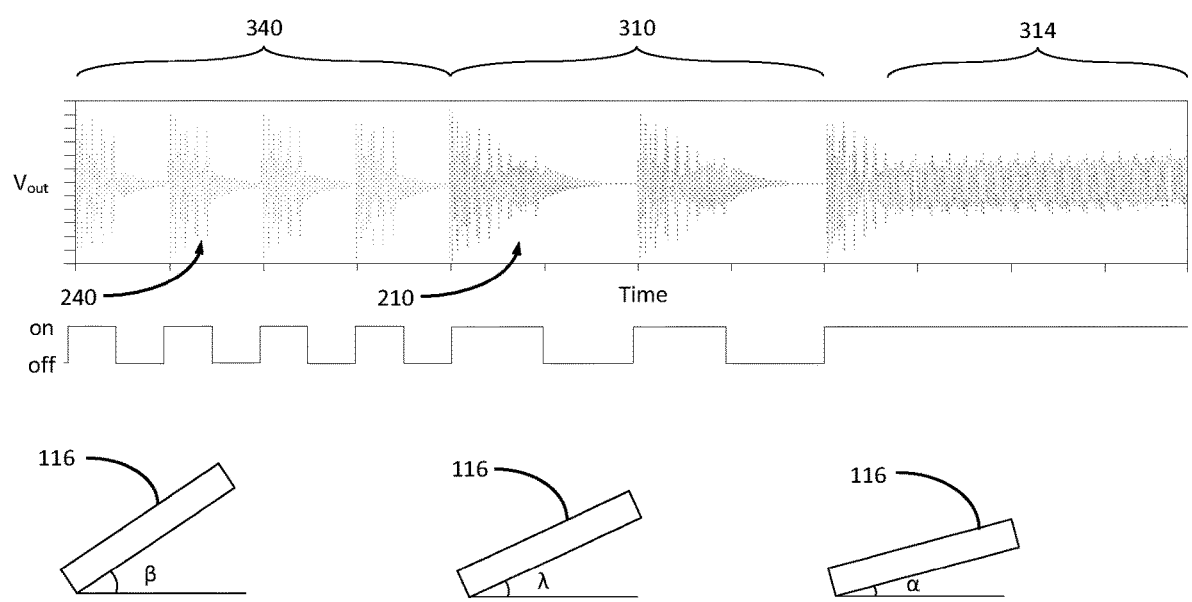
FIG. 3 illustratively depicts a progression of increasing power to the handpiece via an external input.

In addition to driving the handpiece 121 in plurality of on-off cycles 246, all with the same duty cycle but with potentially various duty cycle periods 222 or 252, certain embodiments of the present invention further envision driving the handpiece 121 in a constant on-state modality thereby setting up a sustained emulsification mode. FIG. 3 illustratively depicts a progression of increasing power to the handpiece 121 via an external input. As mentioned earlier, an external input can be accomplished by depressing a foot pedal 116, for example. Taking that into consideration, an operator performing cataract surgery with the handpiece 121 can first cut and break up cataract tissue in a fragmentation mode by maintaining a foot pedal 116 at an angle of β. As an example, for a soft cataract, starting the procedure in emulsification mode may allow the needle 132 to easily penetrate the lens, which may be undesirable if it penetrates too easily/quickly. The fragmentation mode can be accomplished with fragmentation mode on-off pulses 240 having a duty cycle of 50% over a first amount of time 340 (shown here as four fragmentation mode on-off pulses 240). By depressing the foot pedal 116 at a shallower angle of λ, the operator can increase the power of the handpiece 121 into pulsed emulsification mode on-off pulses 210 having the same duty cycle of 50% over second amount of time 310 (shown here as two pulsed emulsification mode on-off pulses 210). By depressing the foot pedal 116 at an even shallower angle of α, the operator can increase the power of the handpiece 121 into a full emulsification mode 214 that is in a constant on-state, which is devoid of any off pulses. As the operator changes the angle of the foot pedal 116 in reverse order (i.e., from α to λ to β, where α is a smaller angle than λ, which is a smaller angle than β) the power of the handpiece 121 decreases from an emulsification mode to a fragmentation mode. In the present embodiment, when in on-off pulse modes (of FIGS. 2A and 2B, for example), fragmentation mode on-off pulses 240 and emulsification mode on-off pulses 210 can be toggled back and forth by changing the duty cycle periods without changing the actual duty cycle.

Figure 4:
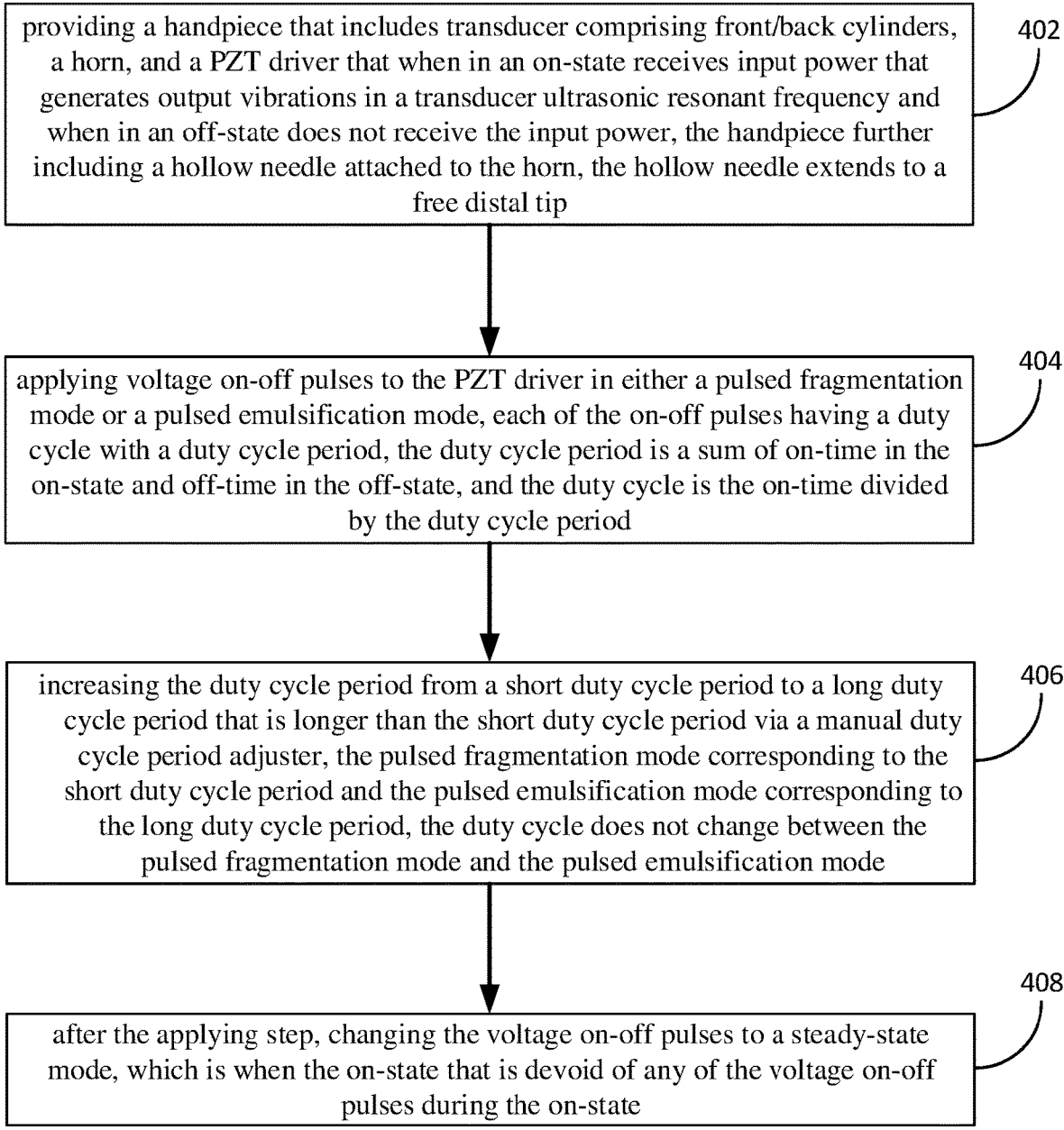
FIG. 4 is a block diagram flowchart of a method for using a cataract surgical instrument consistent with embodiments of the present invention.

FIG. 4 is a block diagram flowchart of a method for using a cataract surgical instrument consistent with embodiments of the present invention. As presented in step 402, a transducer 120 that includes a front/back cylinder 124, a vibration generator 122 and a horn 128 are provided with a hollow needle 132 attached to the horn 128 via a tip hub 134. When in an on-state, the vibration generator 122 generates output vibrations in an ultrasonic frequency and when an off-state does not generate the output vibrations. The ultrasonic frequency is at a resonant frequency of the transducer 120 and in some embodiments is the resonant frequency of the handpiece 121. The hollow needle 132, when attached to the horn 128, is configured to break-up cataractous lens material (of an eye) when energized by the vibration generator 122. The vibration generator 122 outputs vibrations in an ultrasonic frequency at the resonant frequency of the transducer 120, or optionally of the handpiece 121, when in an on-state, i.e., when voltage is applied to the vibration generator 120. An off-state is when there is no voltage applied to the vibration generator 120.

Step 404 is a step for exciting the transducer 120 from a duty cycle fragmentation mode 240 to a duty cycle emulsification mode 210 via a manual duty cycle adjuster, such as a foot pedal 116. Generically speaking, the duty cycle fragmentation mode 240 is at a duty cycle with a short duty cycle period 252 and the duty cycle emulsification mode 210 is at the duty cycle with a long duty cycle period 222 that is longer than the short duty cycle period 252. In the example of FIGS. 2A and 2B, the long duty cycle period 222 is 4 ms. and the short duty cycle period 252 is 2 ms. The duty cycle is defined as a ratio of an on-state time 220 of the on-state divided by a summation time 222 of the on-state 220 and the off-state 221. The duty cycles during the duty cycle fragmentation mode 240 and the duty cycle emulsification mode 210 are all essentially equal, which in the example of FIGS. 2A and 2B is 50%. Certain other embodiments envision a range of duty cycles between 5%-95%, however once a duty cycle is set, it cannot be changed while the handpiece 121 is in operation. These embodiments envision that the duty cycle being changed by an input from a user or operator via manual input/set-up 114 at the controller 110, such as by way of entering in a new duty cycle value via a computer or via an interface or knob at or connected to the controller 110. In this example, when the handpiece 121 is off, or otherwise not engaged in an eye during an eye surgery, the duty cycle may be changed from 50% to 70% for example. This would occur before or after when a handpiece 121 is in operation but not while the handpiece 121 is in operation.

Step 406 is a step for maintaining a steady-state (continuous) emulsification resonance 314 (of FIG. 3) in the transducer 120 via the manual duty cycle adjuster 116, such as depressing the foot pedal 116 at the a angle (of FIG. 3). This is envisioned being done to break up larger lens particles that may be occluding the evacuation orifice 140 at the free distal tip 130 or to more aggressively emulsify lens tissue, such as after cycling the handpiece 121 between the duty cycle fragmentation mode 240 and the duty cycle emulsification mode 210. The continuous emulsification resonance 314 is devoid of any pauses (off times, such as 251 or 221) in the input voltage. In other words, an input voltage (from the power driver 105) to the PZT driver 122 is a continuous voltage that is devoid of any on-off pulses. If an on-off pulse interrupts the continuous emulsification resonance 314, such as by lifting the foot pedal 116 to an λ or β angle, the continuous emulsification resonance 314 can be reinitiated by depressing the foot pedal 116 back to an a angle.

Step 408 is a step for generating only output vibrations of the handpiece 121 in one of the three modes while the handpiece 121 is in operation. The three modes being the duty cycle fragmentation mode 240, the duty cycle emulsification mode 210, or the continuous emulsification mode 314. While in operation, the duty cycle (ration of on-time to cycle period time) does not change.

The method is envisioned to provide flexibility of cutting and fragmenting lens tissue as well as emulsifying harder and larger lens tissue particles while controlling the amount of heat buildup that may damage eye tissue. For example, an eye surgeon may start performing an eye surgery by slowly depressing a foot pedal 116 somewhere between a β to an λ angle to cut cataractous eye tissue in a fragmentation mode. As previously discussed, voltage input from the power driver 105 is delivered to the PZT driver 122 in on-off pulses 246, wherein each of the on-off pulses 246 are at a preset duty cycle, such as a 50% duty cycle. The on-off pulses 246 have a duty cycle period 252 that is sufficiently low to prevent the transducer 120 from reaching resonance thereby keeping the transducer 120 in a sub-resonant vibration mode (i.e., the free distal tip 130 vibrates at a frequency lower than the resonant frequency of the transducer 120 thereby staying in fragmentation mode 240). As shown in FIG. 2A, by pulsing the PZT driver 122 'on' then 'off' then 'on', and so on, a fragmentation mode 240 of the free distal tip 130 is maintained. Certain embodiments envision the eye surgeon being able to adjust the duty cycle period 252 in the fragmentation mode 240 by adjusting the angle of the foot pedal 116 between the β to an λ angle. Certain other embodiments contemplate that there is only one setting and therefore one duty cycle period 252 while in the fragmentation mode 240. Some embodiments envision that during fragmentation mode 240, the frequency of the transducer 120 is lower than the transducer's resonant frequency because the sub-resonant frequency window 242 is not long enough for the transducer 120 to reach resonant frequency before the input voltage is turned off thereby allowing the vibration to decay (the vibration decay zone 244) before the input voltage is turned back on. Certain embodiments envision the frequency of the transducer 120 staying below 20 kHz (in the sonic range) while in fragmentation mode.

Embodiments of the present invention envision the eye surgeon depressing the foot pedal 116 between the λ angle and an a angle to go from pulsed fragmentation mode 240 to pulsed emulsification mode 210. While the duty cycle stays constant (duty cycle percentage does not change), by depressing the foot pedal 116 between λ and α, the eye surgeon can increase the output energy of the transducer 120 by reaching pulsed emulsification mode 210. Pulsed emulsification mode 210 allows enough time for the sub-resonant vibrations to set up at resonance in the transducer 120 (settling time 212) and resonate the transducer 120 for a portion of the on-time 220 in an established resonant frequency zone 214 before power is cut (in the off-time 221). This allows the resonant vibration to decay over the decaying window 216 before power is turned back on (on-time 220). Like the pulsed fragmentation mode 240, the pulsed emulsification mode 210 provides a degree of emulsification while keeping the needle 132 from getting too hot (i.e., hot enough to cause damage to eye tissue).

Embodiments of the present invention further permit the eye surgeon to depress the foot pedal 116 at an α angle to go from pulsed emulsification mode 210 to continuous emulsification mode 314. This is a state that has no pulses but rather allows the transducer 120 to form and hold a continuous resonant frequency until the foot pedal 116 is released, at least somewhat, to go back to angles λ and β. The continuous emulsification mode 314 causes cavitation to break up hard and large lens fragments but can create damaging heat. Certain embodiments envision the resonant frequency of the transducer 120 being above 20 kHz and below 60 kHz.

Figure 5:
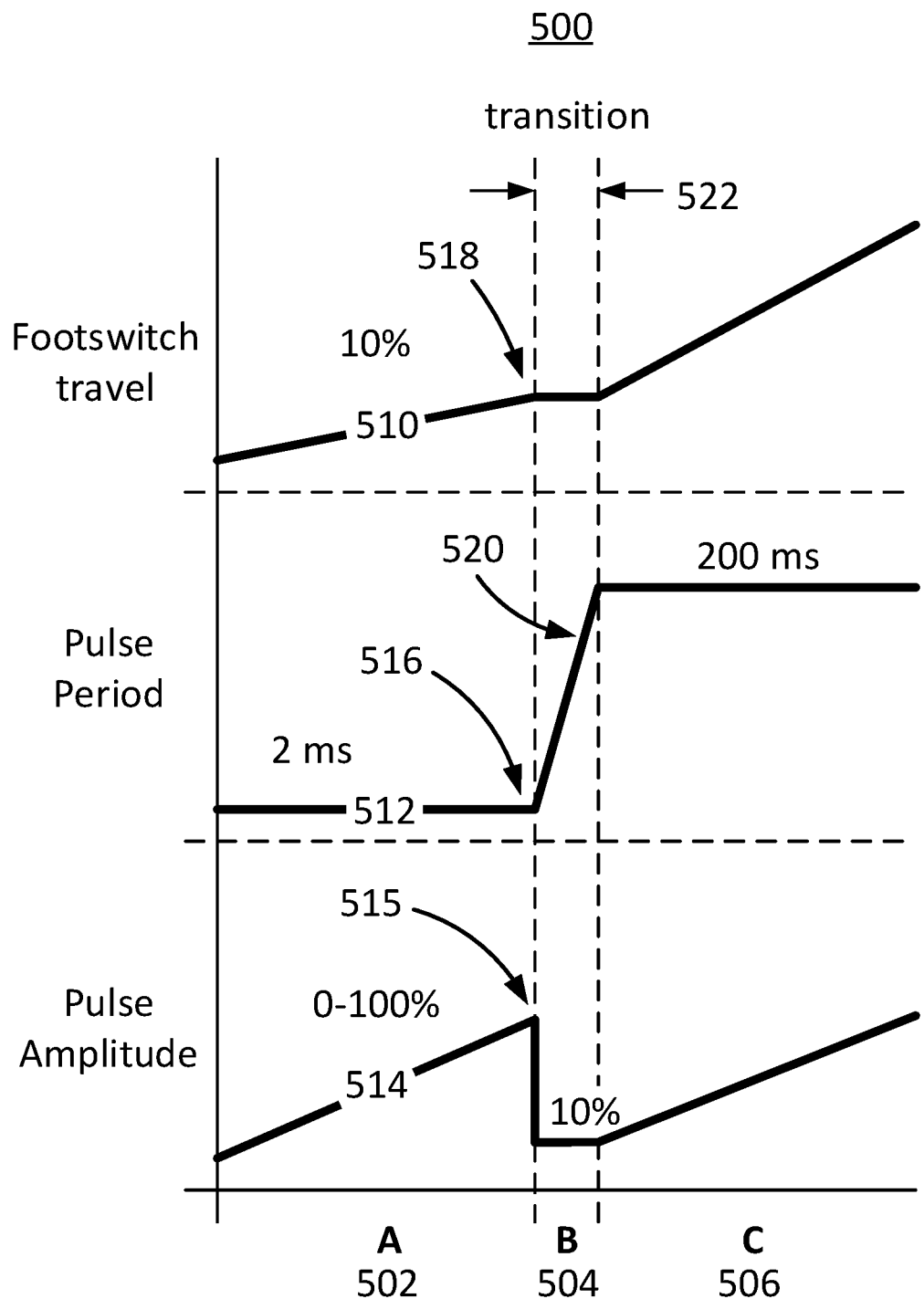
FIG. 5 is a graph depicting embodiments of pulse amplitude, pulse duration, and footswitch travel for a cataract surgical arrangement while in operation consistent with embodiments of the present invention.

FIG. 5 is a graph depicting embodiments of pulse amplitude, pulse duration, and footswitch travel for a cataract surgical arrangement 100 while in operation consistent with embodiments of the present invention. FIG. 5 is described in view of the other figures with some callouts that refer to the other figures. With regards to zone-A 502 and to the footswitch travel chart 510 relative to the pulse amplitude chart 514, as the footswitch (foot pedal) 116 is depressed, the pulse amplitude 514 of the output ultrasonic vibrations that vibrate the transducer 120 (and therefore the needle 132) increase from 0%, when there is no input current to the PZT driver 122, to 100%, which is the maximum fragmentation vibration amplitude 515 in zone-A 502. Though the present depiction is linear, other pulse amplitude curves from start to the maximum 515 are envisioned. In this example, when the maximum fragmentation vibration amplitude 515 is reached in the fragmentation mode of zone-A 502, the foot switch travel 510 is 10%. That is, foot pedal 116 is at a threshold angle between β and λ, which is at a 10% travel. Other embodiments envision the foot switch travel 510 being at a travel percentage that is different than 10% to reach the fragmentation threshold limit 518. Though the present examples depict a foot pedal 116, other embodiments envision the foot switch being a push-button or some other actuating arrangement. While in the fragmentation zone-A 502, the pulse period 512 remains essentially constant, for example 2 ms., though other pulse periods 512 are envisioned so long as resonance does not set up in the transducer 120 (the transducer 120 is not resonating at an ultrasonic frequency).

With reference to the transition zone-B 504, when the foot switch 510 reaches the fragmentation threshold limit 518, certain embodiments envision a transition zone-B 504 for the transducer 120 shifting from the fragmentation mode (of zone-A 502) to an emulsification mode of zone-C 506. In the present example, the pulse amplitude 514 drops to a low or medium level, such as 10%, while the pulse period 512 ramps up to a longer pulse period 512 that allows for ultrasonic resonance to build up, or otherwise establish in the transducer 120. Dropping the pulse amplitude 514 in the transition zone-B 504 is envisioned to manage heat and energy of the vibrating needle 132 as it goes into the higher energy emulsification mode. In the present embodiment, the pulse period in the emulsification mode of zone-C 506 is 200 ms., however other pulse periods are envisioned. Certain embodiments envision the transition time 522 (i.e., time in the transition zone-B 504) preset along with the other parameters, such as pulse amplitude 514 and the pulse period ramp 520 from fragmentation mode to emulsification mode, for example. Hence, when the footswitch travel 510 reaches the threshold 518, the transition zone-B 504 can be a preprogrammed routine that is automatic, i.e., it simply takes over to go into the emulsification mode assuming the surgeon does not back off on the footswitch 116. The transition zone-B 504 ends where the emulsification mode zone-C 506 begins.

With reference to the transition zone-C 506, as the foot switch 116 is depressed, the ultrasonic vibration pulse amplitude 514 increases in the transducer 120 while the pulse period 512 remains constant in the emulsification mode. Certain embodiments envision that as surgeon lets off the foot switch 116, the vibration response in the transducer 120 goes in the reverse direction. I certain embodiments the pulse period stays constant, while in other embodiments it does not. Still other embodiment contemplate the pulse period changing in the transition zone but being constant if not the same in zone-A 502 and zone-C 506.

With the present description in mind, below are some examples of certain embodiments illustratively complementing some of the methods and apparatus embodiments to aid the reader. The elements called out below are examples provided to assist in the understanding of the present invention and should not be considered limiting.

In that light, certain embodiments of the present invention contemplate a cataract surgical instrument 100, as shown in FIG. 1, comprising a handpiece 121 that includes a transducer 120 comprising a front/back cylinders 124, a horn 128, and a PZT driver 122. When the PZT driver 122 is in an on-state, it receives input power (electrical current from an applied voltage) that generates output vibrations in an ultrasonic frequency, thereby driving vibrations in the transducer 120 and ultimately the needle tip 130, which is used as the cutting tool for the cataractous lens) and when in an off-state, the PZT driver 122 does not receive the input power. The ultrasonic frequency is at a resonant frequency of the handpiece 121 to be able to produce high (to near maximum at that frequency) amplitude vibrations in the needle tip 130. A hollow needle 132 is attached to the horn 128. The hollow needle 132 extends to a free distal tip 130 that is configured to penetrate a human eye. A power driver 105 provides the input power to the PZT driver 122 at either 1) a constant on state 314, or 2) a plurality of on-off pulses 246, as shown in FIGS. 2A, 2B and 3. The on-off pulses 246 are either in a pulsed fragmentation mode 240 or a pulsed emulsification mode 210. The on-off pulses 246 each have a duty cycle that is the same in both the pulsed fragmentation mode 240 and pulsed emulsification mode 210. The duty cycle is defined by on-time 250 of the on-state divided by a duty cycle period 222a. For example, in FIG. 2A, the duty cycle period 252 is a sum of the on-time 250 and off-time 251 of the off-state (on-time 250+off-time 251). The pulsed fragmentation mode 240 has a shorter duty cycle period 252 than the pulsed emulsification mode 210.

The cataract surgical instrument 100 embodiment can further be where the transducer 120 is electrically connected to the power driver 105, the power driver 105 is controlled by a controller 110 comprising a processor and non-transitory memory, the non-transitory memory containing computer executable instructions corresponding to the on-off pulses 246 and the processor configured to execute the computer executable instructions that drives the PZT driver 122 via the power driver 105. Optionally, the shorter duty cycle period 252 transitions to the longer duty cycle period 222 because of an external input, wherein the external input is from depressing a foot peddle 116, pressing a button, and/or occlusion blocking a passageway 126 of the hollow needle 132.

The cataract surgical instrument 100 embodiment can additionally be wherein the duty cycle period 222a is between 2 ms-200 ms. Optionally, the duty cycle periods 252 can be configured to increase or decrease by human intervention that can include depressing a switch, such as on the metal shell that encapsulates the front/back cylinders 124.

The cataract surgical instrument 100 embodiment's duty cycle can be between 0.1 and 0.9 (10%-90%).

The cataract surgical instrument 100 embodiment can further include a vacuum line 102 connected to the transducer 120 that is in communication with an evacuation orifice 140 at the free distal tip 130. The vacuum line 102 is configured to suck lens material through the evacuation orifice 140 because the vacuum line 102 has a sub-ambient pressure. In certain embodiments, the shorter duty cycle period 252 transitions to a longer duty cycle period 222 automatically by a drop in the sub-ambient pressure. Optionally, the shorter period 252 transitions to the constant on state 314 automatically by a drop in the sub-ambient pressure.

Yet another embodiment of the present invention envisions a device 100 for cataract surgery (as shown in FIG. 1) generally comprising a handpiece 121 that includes a hollow needle 132 and a transducer 120. The transducer 120 comprising a front/back cylinders 124, a horn 128, and a PZT driver 122. When the PZT driver 122 is in an on-state, it receives input power (current) that generates output vibrations in an ultrasonic frequency but when the PZT driver 122 is in an off-state, it does not receive any input power. In this embodiment, the ultrasonic frequency is at a resonant frequency of the handpiece 121, but in other embodiments the ultrasonic frequency is at a resonant frequency of the transducer 120. The horn 128 can be connected to the hollow needle 132, which extends to a free distal tip 130. The hollow needle 132 is configured to penetrate nothing other than a human eye. A power driver 105 can be connected to the PZT driver 122, which can deliver a plurality of on-off pulses 246 of electrical current to the PZT driver 122 (see FIGS. 2A and 2B). Each of the on-off pulses 246 are defined by a duty cycle period 222a, which is a sum of on-time in the on-state and off-time in the off-state, and a duty cycle, which is the on-time divided by the duty cycle period 222a (on-time/(on-time+off-time)). A manual duty cycle period adjuster, such as a foot pedal 116, can be used to increase the duty cycle period 222a (of the plurality of on-off pulses 246) from that which does not generate an ultrasonic resonance in the handpiece 121 (see the sub-resonant frequency window/zone 242 of FIG. 1A) to that which does generate the ultrasonic resonance in the handpiece 121 (see the established resonant frequency zone 214 of FIG. 2B). In this embodiment, the plurality of on-off pulses 246 all have the same duty cycle while the device 100 is in operation (in operation means while the eye surgeon is actively using the device 100.

The device 100 embodiment for cataract surgery further envisions that the manual duty cycle adjuster comprises a constant on state 314 mode setting that is configured to generate a constant ultrasonic resonant frequency of the handpiece 121 that is devoid of any of the duty cycle periods 246.

The device 100 embodiment for cataract surgery further imagines the transducer 120 being in a pulsed fragmentation mode 240 when the plurality of the on-off pulses have the duty cycle periods 252 that do not generate the ultrasonic resonance in the handpiece 121 and wherein the transducer 120 is in a pulsed emulsification mode 240 when the plurality of the on-off pulses have the duty cycle periods 222 that do generate the ultrasonic resonance in the handpiece 121.

The device 100 embodiment for cataract surgery further envisions that the device 100 can only change the duty cycle when not in operation (not in operation is before or after an eye surgery but not during an eye surgery).

The device 100 embodiment for cataract surgery further envisions the manual duty cycle adjuster being either a handheld adjuster or a foot pedal 116.

Still another embodiment of the present invention envisions a method for using a cataract surgical instrument 100. The cataract surgical instrument 100 generally comprises a handpiece 121 that includes a transducer 120 comprising a front/back cylinders 124, a horn 128, and a PZT driver 122 that when in an on-state receives input power that generates output vibrations in a transducer ultrasonic resonant frequency and when in an off-state does not receive the input power. The handpiece 121 further including a hollow needle 132 that is attached to the horn 128, wherein the hollow needle 132 extends to a free distal tip 130. The method envisions a step for applying voltage on-off pulses 260 to the PZT driver 122 in either a pulsed fragmentation mode 240 or a pulsed emulsification mode 210, wherein each of the on-off pulses 246 have a duty cycle that, in turn, has a duty cycle period 222a. The duty cycle period 222a is a sum of on-time in the on-state and off-time in the off-state and the duty cycle is the on-time divided by the duty cycle period 222a. The duty cycle period 222a is increased from a short duty cycle period 252 to a long duty cycle period 222 that is longer than the short duty cycle period 252 via a manual duty cycle period adjuster. The pulsed fragmentation mode 240 corresponds to the short duty cycle period 252 and the pulsed emulsification mode 210 corresponds to the long duty cycle period 222. The duty cycle does not change between the pulsed fragmentation mode 240 and the pulsed emulsification mode 210. After the applying step, the voltage on-off pulses 246 are changed to a continuous mode 314, which is when the on-state that is devoid of any of the voltage on-off pulses 246 during the on-state.

The method embodiment further contemplates the manual duty cycle adjuster being a foot pedal 116 that lengthens the short duty cycle period 252 to the long duty cycle period 222.

The method embodiment further contemplates depressing the foot pedal 116 to lengthen the short duty cycle period 252 to the long duty cycle period 222.

The method embodiment further contemplates that the the short duty cycle period 252 changes to the long duty cycle period 222 automatically if there is at least a partial occlusion of an evacuation orifice 140 at the free distal tip 130.

The method embodiment further contemplates the short duty cycle period 252 changing to the continuous mode 314 automatically if there is at least a partial occlusion of an evacuation orifice 140 at the free distal tip 130.

Still another embodiment contemplates a device 100 for cataract surgery comprising: a handpiece transducer 120 that includes a PZT driver 122 that when in an off-state does not receive input power but when in an on-state receives the input power that generates output vibrations in the handpiece transducer 120 at an ultrasonic resonant frequency (ultrasonic resonance) of the handpiece transducer 120. A hollow needle 132 extends from the handpiece transducer 120 to a needle free distal tip 130 that is configured to penetrate a human eye. The device 100 further comprises a power driver 105 that delivers a plurality of pulses of electrical current to the PZT driver 122, each of the pulses defined by a duty cycle that occurs over a duty cycle period. For definition purposes, the duty cycle period is a sum of on-time in the on-state 220 and off-time in the off-state 221, and the duty cycle is the on-time divided by the duty cycle period. The device 100 further comprises a manual duty cycle period adjuster 116 that increases the duty cycle period from a fragmentation mode 240, which does not generate the ultrasonic resonance in the handpiece transducer 120, to an emulsification mode 210 that does generate the ultrasonic resonance in the handpiece transducer 120. A transition mode 504 separates the fragmentation handpiece mode 240 and the emulsification mode 210. The duty cycle is constant while the device 100 is in operation.

The cataract surgical instrument 100 further envisioning the transition mode 504 occuring over a transition time 522 in which the duty cycle period when in the fragmentation mode 240 having a first period that ramps to the emulsification mode 210 having a second period, the first period is shorter than the second period.

The cataract surgical instrument 100 further envisioning the duty cycle remaining constant in the transition mode 504.

The cataract surgical instrument 100 further envisioning the transition mode 504 including a preset transition time 522, a preset pulse amplitude, and a preset ramp from the first period to the second period.

The cataract surgical instrument 100 further envisioning the manual duty cycle period adjuster 116 being a foot pedal that starts the transition mode 504 when the foot pedal 116 is depressed at a transition angle. The foot pedal 116 can increase amplitude of the output vibrations in both the fragmentation mode 240 and the emulsification mode 210 when depressed, wherein the transition mode 504 is at a preset amplitude that is constant. In another embodiment, the foot pedal 116 can increase amplitude of the output vibrations in the fragmentation mode 240 from no amplitude, when the foot pedal 116 is not depressed, to a maximum fragmentation mode amplitude 515, when the foot pedal 116 reaches the transition angle. When in the transition mode 504 the output vibrations can be at a preset amplitude that is lower than the maximum fragmentation mode amplitude 515. In yet another optional embodiment, the foot pedal 116 can decrease amplitude of the output vibrations in the emulsification mode 210 to a minimum emulsification mode amplitude when the foot pedal 116 reaches the transition angle 518, wherein when in the transition mode 504 the output vibrations are at a preset amplitude that is at or lower than the minimum emulsification mode amplitude.

The cataract surgical instrument 100 further envisioning the handpiece transducer 120 being connected to a vacuum line 102 that is in communication with an evacuation orifice 140 at the needle free distal tip 130, wherein the vacuum line 102 is configured to suck lens material through the evacuation orifice 140 because the vacuum line 102 is at a sub-ambient pressure. The fragmentation mode 240 can transition to the emulsification mode 210 automatically by a drop in the sub-ambient pressure.

The cataract surgical instrument 100 further envisioning the handpiece transducer 120 being connected to a vacuum line 102 that is in communication with an evacuation orifice 140 at the needle free distal tip 130, wherein the vacuum line 102 is configured to suck lens material through the evacuation orifice 140 because the vacuum line 102 is at a sub-ambient pressure. The fragmentation mode 240 or the emulsification mode 210 transitions to a constant ultrasonic frequency mode 314 at a constant on-state automatically by a drop in the sub-ambient pressure.

In yet another embodiment of the present invention, a device for cataract surgery 100 can comprise a handpiece transducer 120 with a PZT driver 122 connected to a power driver 105 that delivers a plurality of pulses of electrical current to the PZT driver 122, which vibrates the handpiece transducer 120 from a fragmentation mode 240 to an emulsification mode 210 with a transition mode 504 therebetween. The handpiece transducer 120 is configured to vibrate below resonance in the fragmentation mode 240 but at resonance in the ultrasonic mode 210. Each of the pulses is defined by a duty cycle that occurs over a duty cycle period. The duty cycle period is defined as a sum of on-time that a pulse of electrical current is applied to the PZT driver 122 and off-time where the PZT driver 122 is devoid of the electrical current. The duty cycle is the on-time divided by the duty cycle period, wherein the duty cycle remains essentially constant for all the plurality of pulses while the device 100 is in operation.

The device for cataract surgery 100 further envisioning the transition mode 504 occurring over a transition time 522 in which the duty cycle period when in the fragmentation mode 240 having a first period that ramps to the emulsification mode 210 having a second period, the first period is shorter than the second period. The transition mode 504 can include a preset transition time 522, a preset pulse amplitude, and a preset ramp from the first period to the second period.

The device for cataract surgery 100 further envisioning the PZT driver 122 being configured to vibrate the handpiece transducer 120 with output vibrations, wherein a foot pedal 116 connected to the PZT driver 122 that increases amplitude of the output vibrations in both the fragmentation mode 240 and the emulsification mode 210 when depressed. The transition mode 504 can comprise a preset amplitude of the output vibrations that is constant in the transition mode. The transition mode 504 starts when the foot pedal 116 is depressed at a transition angle 518.

The device for cataract surgery 100 further envisions the handpiece transducer 120 being connected to a vacuum line 102 that is in communication with an evacuation orifice 140 at the needle free distal tip 130, wherein the vacuum line 102 is configured to suck lens material through the evacuation orifice 140 because the vacuum line 102 is at a sub-ambient pressure. The fragmentation mode 240 transitions to the emulsification mode 210 automatically by a drop in the sub-ambient pressure.

Still other embodiments of the present invention contemplate a method comprising providing a handpiece transducer 120 with a PZT driver 122 connected to a power driver 105. A hollow needle 132 is inserted into a human eye, wherein the hollow needle 132 extends from the handpiece transducer 120. A plurality of pulses of electrical current is delivered to the PZT driver 122 via the power driver 105, wherein the pulses of electrical current generate output vibrations in the handpiece transducer 120. The handpiece transducer 120 can be made to vibrate below resonance of the handpiece transducer 120 with the output vibrations (fragmentation mode 240). The handpiece transducer 120 can be made to vibrate at resonance of the handpiece transducer 120 with the output vibrations (emulsification mode 210). Each of the pulses is defined by a duty cycle that occurs over a duty cycle period that is longer in the emulsification mode 210 than the fragmentation mode 240. The duty cycle period is defined as a sum of on-time that a pulse of electrical current is applied to the PZT driver 122 and off-time where the PZT driver 122 is devoid of the electrical current. The duty cycle is the on-time divided by the duty cycle period. The duty cycle remains essentially constant for all of the plurality of pulses while the device 100 is in operation. A foot pedal 116 connected to the PZT driver 122 can be depressed, or pushed down, from a first position to a second position 518, wherein the second position 518 defines an upper amplitude threshold of the output vibrations in the fragmentation mode 240. A transition zone 504 is entered by depressing the foot pedal 116 beyond the second position 518, wherein the transition zone 504 lengthens the duty cycle period from that of the fragmentation mode 240 to the emulsification mode 210.

The method embodiment further contemplates the transition zone 504 having a preset transition time 522, a preset pulse amplitude, and a preset ramp from a short period in the fragmentation mode 240 to a long period in the emulsification mode 210.

The method embodiment further envisions the fragmentation mode 504 transitioning to the emulsification mode 240 automatically if the hollow needle 132 is at least partially occluded.

The method embodiment further contemplates the foot pedal 116 being depressed to a third position that increases amplitude of the output vibrations in the emulsification mode 210.

The method embodiment further contemplates changing from either the fragmentation mode 240 or the emulsification mode 210 to a continuous mode 314 automatically if there is at least a partial occlusion of an evacuation orifice 140 at the free distal tip 130, wherein the continuous mode 504 is when the electrical current that is applied to the PZT driver 122 devoid of pulses.

The above sample embodiments should not be considered limiting to the scope of the invention whatsoever because many more embodiments and variations of embodiments are easily conceived within the teachings, scope and spirit of the instant specification.

It is to be understood that even though numerous characteristics and advantages of various embodiments of the present invention have been set forth in the foregoing description, together with the details of the structure and function of various embodiments of the invention, this disclosure is illustrative only, and changes may be made in detail, especially in matters of structure and arrangement of parts within the principles of the present invention to the full extent indicated by the broad general meaning of the terms used herein. For example, though embodiments of the present invention describe a fragmentation mode 'short' pulsed period 252 being 2 ms. (1 ms. 'on' and 1 ms. 'off'), other short periods can be used so long as an ultrasonic frequency resonance is not set up in the transducer 120 without departing from the scope and spirit of the present invention. Likewise, other emulsification mode 'long' pulses can be used other than the 'long pulsed period 222 of 4 ms without departing from the scope and spirit of the present invention. It should also be appreciated that the appropriate mechanical and electrical components as well as the appropriate software not discussed in detail in the present disclosure must be implemented in accordance known to those skilled in the art. The specification and drawings are to be regarded as illustrative and exemplary rather than restrictive. For example, the word "preferably," and the phrase "preferably but not necessarily," are used synonymously herein to consistently include the meaning of "not necessarily" or optionally. "Comprising," "including," and "having," are intended to be open-ended terms.

It will be clear that the claimed invention is well adapted to attain the ends and advantages mentioned as well as those inherent therein. While presently preferred embodiments have been described for purposes of this disclosure, numerous changes may be made which readily suggest themselves to those skilled in the art and which are encompassed in the spirit of the claimed invention disclosed and as defined in the appended claims. Accordingly, it is to be understood that even though numerous characteristics and advantages of various aspects have been set forth in the foregoing description, together with details of the structure and function, this disclosure is illustrative only, and changes may be made in detail, especially in matters of structure and arrangement to the full extent indicated by the broad general meaning of the terms in which the appended claims are expressed.

What is claimed is:

1. A device for cataract surgery comprising:
a handpiece that includes a PZT driver, a front cylinder, a back cylinder, and a horn, the PZT driver that when in an off-state is devoid of input power but when in an on-state has the input power, the input power is configured to generate output vibrations in the handpiece at an ultrasonic resonant frequency (ultrasonic resonance) of the handpiece;
a hollow needle extending from the handpiece to a needle free distal tip that is configured to penetrate a human eye;
a power driver that delivers a plurality of pulses of electrical current to the PZT driver, each of the pulses defined by a duty cycle that occurs over a duty cycle period, the duty cycle period is a sum of on-time in the on-state and off-time in the off-state, and the duty cycle is the on-time divided by the duty cycle period;
a manual duty cycle period adjuster configured to increase the duty cycle period from a fragmentation mode, which does not generate the ultrasonic resonance in the handpiece, to an emulsification mode that does generate the ultrasonic resonance in the handpiece,
a transition mode separates the fragmentation handpiece mode and the emulsification mode, the duty cycle is constant while the device is in operation.

2. The cataract surgical instrument of claim 1, wherein the transition mode occurs over a transition time in which the duty cycle period when in the fragmentation mode having a first period that ramps to the emulsification mode having a second period, the first period is shorter than the second period.

3. The cataract surgical instrument of claim 2, wherein the duty cycle remains constant in the transition mode.

4. The cataract surgical instrument of claim 2, wherein the transition mode includes a preset transition time, a preset pulse amplitude, and a preset ramp from the first period to the second period.

5. The cataract surgical instrument of claim 1, wherein the manual duty cycle period adjuster is a foot pedal that starts the transition mode when the foot pedal is depressed at a transition angle.

6. The cataract surgical instrument of claim 5, wherein the foot pedal increases amplitude of the output vibrations in both the fragmentation mode and the emulsification mode when depressed, the transition mode is at a preset amplitude that is constant.

7. The cataract surgical instrument of claim 5, wherein the foot pedal increases amplitude of the output vibrations in the fragmentation mode from no amplitude, when the foot pedal is not depressed, to a maximum fragmentation mode amplitude, when the foot pedal reaches the transition angle, when in the transition mode the output vibrations are at a preset amplitude that is lower than the maximum fragmentation mode amplitude.

8. The cataract surgical instrument of claim 5, wherein the foot pedal decreases amplitude of the output vibrations in the emulsification mode to a minimum emulsification mode amplitude when the foot pedal reaches the transition angle, when in the transition mode the output vibrations are at a preset amplitude that is at or lower than the minimum emulsification mode amplitude.

9. The cataract surgical instrument of claim 1, wherein the handpiece is connected to a vacuum line that is in communication with an evacuation orifice at the needle free distal tip, the vacuum line is configured to suck lens material through the evacuation orifice because the vacuum line is at a sub-ambient pressure, the fragmentation mode transitions to the emulsification mode automatically by a drop in the sub-ambient pressure.

10. The cataract surgical instrument of claim 1, wherein the handpiece is connected to a vacuum line that is in communication with an evacuation orifice at the needle free distal tip, the vacuum line is configured to suck lens material through the evacuation orifice because the vacuum line is at a sub-ambient pressure, the fragmentation mode or the emulsification mode transitions to a constant ultrasonic frequency mode at a constant on-state automatically by a drop in the sub-ambient pressure.

11. A device for cataract surgery comprising:
a handpiece that includes a PZT driver, a front cylinder, a back cylinder, and a horn, the PZT driver connected to a power driver configured to deliver a plurality of pulses of electrical current to the PZT driver which vibrates the handpiece from a fragmentation mode to an emulsification mode with a transition mode therebetween,
the handpiece configured to vibrate below resonance of the handpiece in the fragmentation mode but at resonance of the handpiece in an ultrasonic mode,
each of the pulses defined by a duty cycle that occurs over a duty cycle period,
the duty cycle period is defined as a sum of on-time that a pulse of electrical current is applied to the PZT driver and off-time where the PZT driver is devoid of the electrical current,
the duty cycle is the on-time divided by the duty cycle period,
the duty cycle remains essentially constant for all the plurality of pulses while the device is in operation.

12. The device for cataract surgery of claim 11, wherein the transition mode occurs over a transition time in which the duty cycle period when in the fragmentation mode having a first period that ramps to the emulsification mode having a second period, the first period is shorter than the second period.

13. The device for cataract surgery of claim 12, wherein the transition mode includes a preset transition time, a preset pulse amplitude, and a preset ramp from the first period to the second period.

14. The device for cataract surgery of claim 11, wherein the PZT driver is configured to vibrate the handpiece with output vibrations, a foot pedal connected to the PZT driver configured to increase amplitude of the output vibrations in both the fragmentation mode and the emulsification mode when depressed, the transition mode comprising a preset amplitude of the output vibrations that is constant in the transition mode, the transition mode configured to start when the foot pedal is depressed at a transition angle.

15. The device for cataract surgery of claim 11, wherein the handpiece is connected to a vacuum line that is in communication with an evacuation orifice at the needle free distal tip, the vacuum line is configured to suck lens material through the evacuation orifice because the vacuum line is at a sub-ambient pressure, the fragmentation mode transitions to the emulsification mode automatically by a drop in the sub-ambient pressure.

16. A method comprising:
providing a handpiece comprising a PZT driver, a front cylinder, a back cylinder, and a horn, the PZT driver connected to a power driver,
inserting a hollow needle into a human eye, the hollow needle extending from the handpiece;
delivering a plurality of pulses of electrical current to the PZT driver via the power driver, the pulses of electrical current generate output vibrations in the handpiece;
vibrating the handpiece transducer below resonance of the handpiece transducer with the output vibrations (fragmentation mode);
vibrating the handpiece transducer at resonance of the handpiece transducer with the output vibrations (emulsification mode),
each of the pulses defined by a duty cycle that occurs over a duty cycle period that is longer in the emulsification mode than the fragmentation mode,
the duty cycle period is defined as a sum of on-time that a pulse of electrical current is applied to the PZT driver and off-time where the PZT driver is devoid of the electrical current,
the duty cycle is the on-time divided by the duty cycle period,
the duty cycle remains essentially constant for all the plurality of pulses while the device is in operation;
depressing a foot pedal connected to the PZT driver from a first position to a second position, the second position defines an upper amplitude threshold of the output vibrations in the fragmentation mode; and
entering a transition zone by depressing the foot pedal beyond the second position, the transition zone lengthens the duty cycle period from that of the fragmentation mode to the emulsification mode.

17. The method of claim 16, wherein the transition zone has a preset transition time, a preset pulse amplitude, and a preset ramp from a short period in the fragmentation mode to a long period in the emulsification mode.

18. The method of claim 16, wherein the fragmentation mode transitions to the emulsification mode automatically if the hollow needle is at least partially occluded.

19. The method of claim 16, depressing the foot pedal to a third position that increases amplitude of the output vibrations in the emulsification mode.

20. The method of claim 16 changing from either the fragmentation mode or the emulsification mode to a continuous mode automatically if there is at least a partial occlusion of an evacuation orifice at the free distal tip, the continuous mode is when the electrical current that is applied to the PZT driver devoid of pulses.

* * * * *